United States Patent [19]
Yu

[11] Patent Number: 5,698,085
[45] Date of Patent: Dec. 16, 1997

[54] COATING ANALYSIS APPARATUS

[75] Inventor: George T. Yu, Tao-Yuan Hsien, Taiwan

[73] Assignee: National Science Council, Taiwan

[21] Appl. No.: 399,367

[22] Filed: Mar. 6, 1995

[51] Int. Cl.[6] .................................................. G01N 27/26
[52] U.S. Cl. ...................... 204/434; 204/404; 205/776.5; 205/791
[58] Field of Search ............................... 204/434, 406; 205/791

[56] References Cited

U.S. PATENT DOCUMENTS

| | | | |
|---|---|---|---|
| 2,568,713 | 9/1951 | Brenner | 204/434 |
| 3,356,597 | 12/1967 | Schmidt | 204/434 |
| 4,647,365 | 3/1987 | Irlesberger et al. | 204/434 |

OTHER PUBLICATIONS

Webster's Seventh New Collegiate Dictionary, 1963, p. 987.

Primary Examiner—T. Tung
Attorney, Agent, or Firm—Michael D. Bednarek; Kilpatrick Stockton LLP

[57] ABSTRACT

A coating analysis apparatus is suitable for analyzing four physical properties including the internal stress of a coating, the thickness of a coating, the current efficiency of electroplating and the corrosion rate of a coating. The apparatus comprises a testing cell filled with an electrolyte solution or an electroplating solution; a programmable power supply for supplying power to electroplate or electrolyze a specimen; and a microprocessor for controlling the programmable power supply to supply the power and analyzing the four physical properties.

1 Claim, 4 Drawing Sheets

COATING ANALYSIS APPARATUS

BACKGROUND OF THE INVENTION

1. Field of the Invention

The present invention relates to a coating analysis apparatus, especially to a coating analysis apparatus for analyzing the internal stress of a coating, the current efficiency of electroplating, the thickness of a coating, and the corrosion rate of a coating (or metal, alloy).

2. Description of Prior Art

The properties of a coating, such as its internal stress, current efficiency, thickness, and corrosion rate, have been analyzed previously. However, conventional coating analysis apparatuses can merely analyze one of these properties at a time. Also, conventional apparatuses are subject to certain problems. The background of the present invention is separately introduced in the following four parts:

3. Internal Stress of A Coating

A spiral contractometer for measuring the internal stress of a coating was developed by Brenner (U.S. Pat. No. 2,568,713), and was widely applied later. However, some limitations of these spiral contractometers have be noted. These problems include low precision, long testing time, a need for a large amount of test solution, and difficulty with preparing specimens. Furthermore, the spiral contractometer can not monitor the measuring processes. Irlesberger (U.S. Pat. No. 4,647,365) developed a stress monitoring apparatus including a strain gauge and a strain sensor for sensing the strain within a coating. In this arrangement, the internal stress within a coating is found by means of magnifying and transforming a strain signal generated by the strain sensor. Unfortunately, users always think that mounting the strain gauge is troublesome. Besides, the stress monitoring apparatus can be very susceptible to noise interference. Engelhaupt chose a pressure sensor for sensing the internal stress within a coating (U.S. Pat. No. 4,986,130). However, a simpler and more sensitive arrangement would be desired.

4. Thickness of Coating

Grower was the first to demonstrate the feasibility of determining the thickness of oxidizable or reducible coatings on metals (G. G. Grower, Proc. Am. Soc. Testing Materials, 17, 129 (1917)). In Grower's method, which may be regarded as the first reported coulometric titration, the coating is oxidized at a more or less controlled potential, and the quantity of electricity consumed in this process is measured with a water coulometer. The completion of dissolution is determined by following the potential of the metallic specimen during electrolysis. Application was made by Grower to the measurement of the thickness of tin coatings on copper.

Grower's method was greatly improved by Evans and his colleagues, who maintained the electrolysis current at a constant intensity (U. R. Evans and L. C. Bannister, Proc. Roy. Soc. (London) A125, 370 (1929)). Application of this improved method has been made to determine the thickness of films of corrosion products on metals and to analyze metallic coatings. The film is oxidized or reduced at constant current, and the potential of the metal is measured during electrolysis. The completion of dissolution of the film is indicated by a rapid variation of the potential. The method is very sensitive, and films having a thickness of only a few angstroms can be measured. The evolution of hydrogen at sufficiently cathodic potentials limit somewhat the usefulness of the method, although this difficulty could possibly be overcome by the use of perfectly anhydrous solvents.

Recently Edward P. Harbulak (U.S. Pat. No. 4,310,389) developed an apparatus for measuring the thickness of individual layers of a multilayer plated deposit. A problem with this arrangement is that the measuring process is manually carried out. A computer is required in order to pursue accurate measuring results.

Current Efficiency of Electroplating

Generally speaking, the current efficiency of electroplating is always less than 100%. To reach 100%, electric leakage and side reaction would not be allowed during the electroplating process. It is possible to avoid electric leakage. However, the side reaction is ultimately unavoidable because the electroplating always proceeds in the water solution.

GB 1,274,892, U.S. Pat. No. 3,632,488, U.S. Pat. No. 3,712,857, and U.S. Pat. No. 3,751,355 are examples of prior art current efficiency measurement schemes. However, these patents cannot lead to very accurate measuring results because it is hard to control the factors affecting current efficiency of electroplating, such as temperature, flow speed, concentration, and some physical properties of sensor elements.

Corrosion Rate of a Coating

Two methods, a weight loss method and an electrochemical method, are widely utilized for measuring the corrosion rate of a coating. However, these two methods have their respective drawbacks. The weight loss method takes a long time to measure the corrosion rate of a coating. It is worse in the condition of low corrosion rate. Besides, the weight loss method is nearly ineffective if the corrosion rate of coating is not constant. The electrochemical method is more popular than the weight loss method. The main reason for this is that the electrochemical method takes a much shorter time to measure the corrosion rate of the coating. Furthermore, researchers can utilize the electrochemical method to find corrosion reaction mechanisms. However, researchers need to manually analyze the polarization curve on paper while using the electrochemical method to find the corrosion rate of a coating. This may possibly lead to an inaccurate analyzing result. To avoid such a problem, many computerized systems for analyzing the corrosion rate of a coating have been developed. Unfortunately, the computerized systems are unable to obtain a linearization polarization curve at high voltage because the polarization curve has been already distorted.

All of the above problems are solved in this invention. This invention, concerning the corrosion rate of a coating, is based the following prior arts: (1) C. Wagner and W. Z. Trand, Electrochem, 44 (1938), P.391, (2) C. Kasper, Trans. ECS 77 (1940), P.353, (3) M. Stern and A. L. Geary, J. Electrochem. Soc. 104 (1957), P.56, (4) Evans, U. R., "The corrosion and oxidation of metals", Arnold (1961), (5) Cao Chu-Nan, Corros. Sci. vol.22, P.205, 1982, (6) R. S. Munn, O. F. Devereux, "Numerical Modeling and Solution of Galvanic Corrosion System: Part 1 Governing Differential Equation and Electronic Boundary Conditions", Corrosion 47, 8 (1991), P.612, and (7) J. O. M. Bockris, Modern Electrochemistry, Vo.12, Chap.8. These references will be mentioned again in the later preferred embodiment.

SUMMARY OF THE INVENTION

An primary object of the present invention is to provide a coating analysis apparatus for multifunctionally analyzing four physical properties including the internal stress of a coating, the current efficiency of electroplating, the thickness of a coating and the corrosion rate of a coating.

A secondary object of the present invention is to provide an apparatus for analyzing a coating. The apparatus gives fast, simple and accurate coating analysis.

In accordance with the objects of the present invention, there is provided a coating analysis apparatus for analyzing internal stress within the coating on one surface of a specimen with an electroplating solution. The coating analysis apparatus for analyzing internal stress comprises a testing cell filled with the electroplating solution; a fixture mounted in the testing cell for fixing one lend of the specimen to let the other end of the specimen be a free end; a metal plate mounted in the testing cell; a programmable power supply having a positive terminal coupled with the metal plate and a negative terminal coupled with the specimen for supplying current to electroplate the specimen; a noncontact displacement sensor mounted beside the free end of the specimen and coupled with the programmable power supply for sensing displacement of the free end of the specimen and generating and sending a displacement signal to the programmable power supply; and a microprocessor coupled with the programmable power supply for controlling the programmable power supply to supply the current and receiving the displacement signal from the programmable power supply and calculating the internal stress within the coating.

Alternatively, there is provided a coating analysis apparatus for analyzing the thickness of coatings of a specimen with an electrolyte solution. The coating analysis apparatus for analyzing the coating thickness comprises a testing cell placed on the specimen and filled with the electrolyte solution touching the coating; an auxiliary electrode mounted in the testing cell; a programmable power supply, having a positive terminal coupled with the specimen to make it an anode and a negative terminal coupled with the auxiliary electrode to make it a cathode, for supplying constant current to dissolve the coatings and converting potential between the anode and the cathode to a potential signal; and a microprocessor coupled with the programmable power supply for controlling the programmable power supply to supply the constant current, for receiving the potential signal from the programmable power supply, for counting the dissolving period of each coatings by analyzing the potential signal and for calculating the thickness of the coatings based on the dissolving period of each coatings.

Alternatively, there is provided a coating analysis apparatus for analyzing the current efficiency of electroplating with an electroplating solution, an electrolyte solution and a specimen which is electroplated to form a coating thereon and then electrolyzed to dissolve the coating. The coating analysis apparatus for analyzing the current efficiency comprises a testing cell placed on the specimen and filled with the electroplating solution in an electroplating process and filled with the electrolyte solution in an electrolyzing process; an auxiliary electrode mounted in the testing cell; a programmable power supply, having a positive terminal coupled with the auxiliary electrode in the electroplating process and coupled with the specimen in the electrolyzing process to make each an anode, and a negative terminal coupled with the specimen in the electroplating process and coupled with the auxiliary electrode in the electrolyzing process to make each a cathode, for supplying constant current $I_{const}$ to electroplate the specimen so that the specimen is covered with the coating in the electroplating process and supplying the same constant current $I_{const}$ to dissolve the coating and converting potential between the anode and the cathode to a potential signal in the electrolyzing process; and a microprocessor coupled with the programmable power supply for controlling the programmable power supply to supply the constant current $I_{const}$ to electroplate the specimen for a predetermined period $T_c$ in the electroplating process and to dissolve the coating for a period $T_a$ in the electrolyzing process, for receiving the potential signal from the programmable power supply, for counting the period $T_a$ by analyzing the potential signal, and for calculating the current efficiency based on the predetermined period $T_c$ and the period $T_a$.

Alternatively, there is provided a coating analysis apparatus for analyzing the corrosion rate of a specimen with a corrosion solution. The coating analysis apparatus for analyzing the corrosion rate comprises a testing cell put on the specimen and filled with the corrosion solution touching the specimen; an auxiliary electrode mounted in the testing cell; a programmable power supply, having a positive terminal coupled with the auxiliary electrode and a negative terminal coupled with the specimen so that the programmable power supply, the auxiliary electrode, the electrolyte solution and the specimen form a circuit, for supplying the circuit with potential and detecting current in the circuit and generating a current signal; and a microprocessor coupled with the programmable power supply for controlling the programmable power supply to vary the potential at a predetermined rate and receiving the current signal from the programmable power supply as well as calculating the Tafel extrapolation corrosion current, linear polarization corrosion current and polarization resistance corrosion current.

DETAILED DESCRIPTION OF THE PREFERRED EMBODIMENT

A coating analysis apparatus according to this invention can multifunctionally analyze four physical properties including the internal stress of a coating, the current efficiency of electroplating, the thickness of a coating, and the corrosion rate of a coating. All analyzing programs stored in a PC computer (or floppy disks) of the apparatus are written with the macro instructions of LOTUS 1-2-3 (please refer to attached documents 1–4). Furthermore, the auxiliary electrode of the apparatus is a passive electrode, such as a platinum electrode. The apparatus for analyzing coatings is respectively discussed in detail in the following four sections.

The Internal Stress of a Coating

Figure 1:
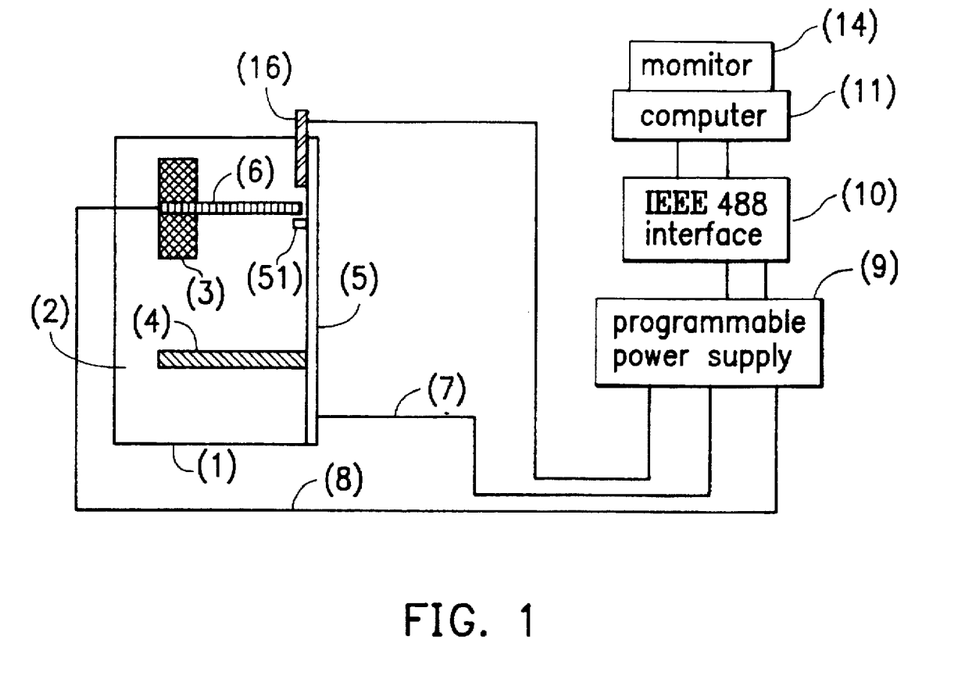
FIG. 1 shows a coating analysis apparatus for analyzing the internal stress of a coating according to this invention.

FIG. 1 shows a coating analysis apparatus for analyzing the internal stress of a coating according to this invention. A testing cell (1), with a fixture (3) and a metal plate (4)

mounted therein, is utilized to electroplate a specimen (6). One surface of the specimen (6) is insulated and the other surface is not. Furthermore, one end of the specimen (6) is fixed by the fixture (3) and the other end remains free. The free end of the specimen (6) has a predetermined distance from a vernier (51) of a vernier scale (5) which is mounted beside the testing cell (1) and touches the metal plate (4). A noncontact displacement sensor (16) is located close to the specimen (6) for sensing the displacement of the free end of the specimen (6) and generating a displacement signal during an electroplating process.

An IEEE 488 interface (10) is connected between a programmable power supply (9) and a computer (11) provided with a monitor (14), wherein the programmable power supply (9) is electrically connected to the noncontact displacement sensor (16) so that the computer (11) receives the displacement signal of the free end of the specimen (6) from the noncontact displacement sensor (16). Furthermore, a negative terminal of the programmable power supply (9) is electrically connected to the specimen (6) through a cathode conducting wire (8) to make the specimen a cathode, while a positive terminal of the programmable power supply (9) is electrically connected to the vernier scale (5) through an anode conducting wire (7) to make a metal plate (4) an anode plate. At last, the testing cell (1) is filled with an electroplating solution (2). The programmable power supply (9), the anode conducting wire (7), the vernier scale (5), the metal plate (4), the electrolyte solution (2), the specimen (6) and the cathode conducting wire (8) thus form a circuit.

During the electroplating process, the computer (11) controls the programmable power supply (9) through the IEEE 488 interface (10) to supply current for electroplating the specimen (6) and detects the potential between the anode and the cathode. The specimen (6) is only electroplated on the surface without insulation. That is, there is a coating formed on the surface without insulation. Thus, internal stress occurs within the coating of the specimen (6) to make the specimen (6) gradually deform. On the other hand, the noncontact displacement sensor (16) senses the displacement of the free end of the specimen (6) and sends a displacement signal to the computer (11) through the programmable power supply (9) and the IEEE 488 interface (10), and the computer (11) uses the following formulas [1], [2] and [3] to calculate the internal stress within the coating and show the results on the monitor (14).

$$S=(f/t)\cdot[E_0 t_0^2+Et t_0(4+6t)/(t_0+3t^2 t_0^{-2})/(3L^2/(1+5t/3t_0))] \quad [1]$$

$$Si=(df/dt)\cdot[E_0 t_0^2+Et t_0(4+6t)/(t_0+3t^2 t_0^{-2})/(3L^2/(1+5t/3t_0))] \quad [2]$$

$$t=(A\cdot I\cdot T\cdot CE)/(Z\cdot F\cdot D\cdot L\cdot W) \quad [3]$$

wherein S is the internal stress;
Si is the momentary internal stress;
t is the coating thickness;
$t_0$ is the specimen thickness;
E is the elastic coefficient of the coating;
$E_0$ is the elastic coefficient of the specimen;
L is the length of the specimen;
W is the width of the specimen;
A is the atomic weight of the coating;
Z is the valence of the coating;
F is the Faraday constant;
D is the density of the coating;
T is the electroplating time;

CE is the current efficiency;
I is the current;
f is the displacement of the free end of the specimen.

The specimen (6) deforms more and more and finally touches the vernier (51) so that the programmable power supply (9), the anode conducting wire (7), the vernier scale (5), the specimen (6) and the cathode conducting wire (8) form a short circuit. Thus, the potential between the anode and the cathode suddenly drops. The computer (11) cuts off power supply through the IEEE 488 interface (10) to end the electroplating process as soon as the computer (11) detects the sudden drop in the potential.

A program stored in the computer for detecting the potential between the anode and the cathode, measuring and calculating the internal stress within the coating, is shown in attached document 1.

EXAMPLE 1

The electroplating solution contains 300 g/l $NiSO_4 \cdot 6H_2O$ and 35 g/l $H_3BO_3$. Execute the program stored in the computer and input the following parameters to the computer:

the specimen thickness 0.25 mm,
length 42 mm,
width 7 mm,
elastic coefficient 124000 $MN/m^2$,
the current efficiency 95%,
density 1 $A/dm^2$,
the Faraday constant 96487 coul,
the nickel coating atomic weight 58.7 g/mole,
density 8.9 $g/cm^3$,
valence 2,
elastic coefficient 204000 $MN/m^2$.

Figure 2:
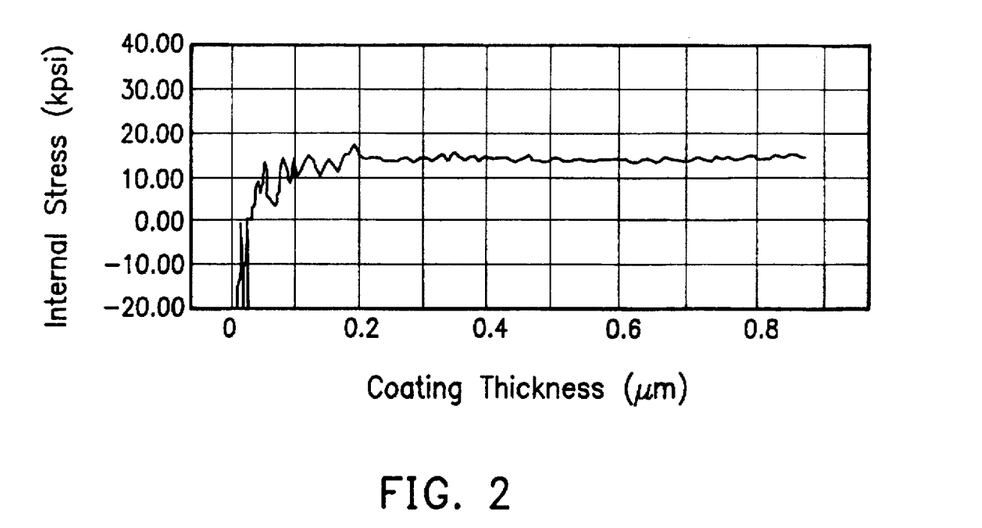
FIG. 2 shows the curve of the internal stress of the coating relative to the coating thickness in example 1.
Figure 3:
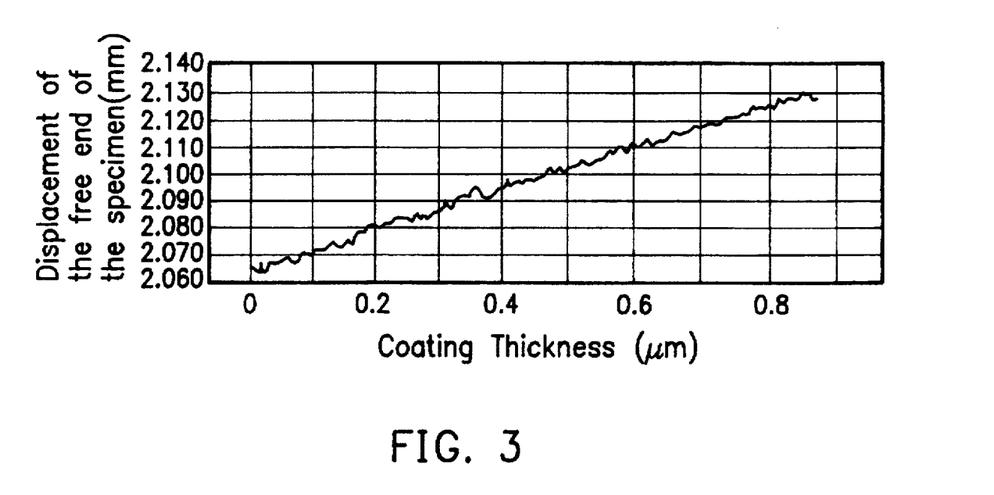
FIG. 3 shows the curve of the displacement of the free end of the specimen relative to the coating thickness in example 1.

FIG. 2 shows the curve of the internal stress of the coating relative to the coating thickness. FIG. 3 shows the curve of the displacement of the free end of the specimen relative to the coating thickness. As a result, the internal stress within the coating is 15.276 kpsi in tension after 258 seconds.

The Coating Thickness

In this embodiment, a constant current is utilized to dissolve coatings (or a coating) in an electrolyte solution. Whenever each layer of the coatings entirely dissolves, the corresponding potential obviously varies. Then, a computer uses the following formula [4] to calculate the corresponding coating thickness.

$$d=(A\cdot I\cdot T\cdot CE)/(96487\cdot n\cdot D\cdot Area) \quad [4]$$

wherein
d is the coating thickness,
A is the atomic weight of the coating,
I is the current,
T is the electrolyzing period of the coating,
CE is the current efficiency,
n is the valence of the coating,
D is the density of the coating,
Area is the testing area of a specimen.

Figure 4:
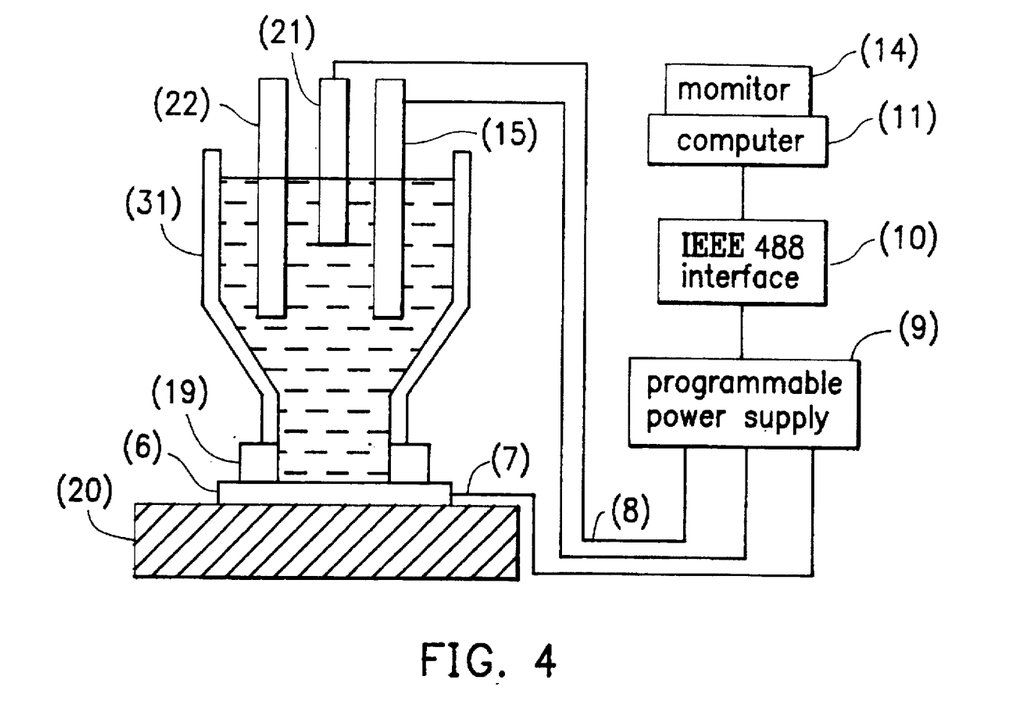
FIG. 4 shows a coating analysis apparatus for analyzing the coating thickness according to this invention.

FIG. 4 shows a coating analysis apparatus for analyzing the coating thickness according to this invention. A specimen (6) is put on a worktable (20), while the upper surface of the specimen (6) is covered with coatings. A testing cell (31) is put on the specimen (6) with an insulating gasket (19) mounted on its bottom. The size of the insulating gasket (19) can determine the measured area of the specimen (6).

A positive terminal of a programmable power supply (9) is electrically connected to the specimen (6) through an anode conducting wire (7) to make this specimen an anode, while an auxiliary electrode (21) is put in the testing cell (31) and made a cathode by electrical connection to a negative terminal of the programmable power supply (9) through a cathode conducting wire (8). Also, a reference electrode (15) is put in the testing cell (31) and electrically connected to the programmable power supply (9) to supply a reference potential with respect to both the anode and the cathode. An IEEE 488 interface (10) is electrically connected between the programmable power supply (9) and a computer (11). The computer (11) is provided with a monitor (14) for showing the measuring results. After the above arrangement is complete, the testing cell (31) is filled with electrolyte solution.

During the electrolyzing process, the computer (11) controls the programmable power supply (9) through the IEEE 488 interface (10) to supply constant current to dissolve the coatings on the specimen (6). At the same time, the programmable power supply (9) transfers the potential between the cathode and the anode to a potential signal and sends the potential signal to the computer (11) through the IEEE 488 interface (10). As mentioned above, each layer of the coatings entirely dissolving will make the potential between the cathode and the anode vary a lot (the potential at the moment is called polarization potential). Therefore, the computer (11) can calculate the electrolyzing period of each coating by analyzing the potential signal. Furthermore, the computer (11) can use the electrolyzing period to calculate each coating thickness based on the formula (4) and show the calculated results on the monitor (14). A program stored in the computer (11) for analyzing the coating thickness is shown in attached document 2.

Sometimes a passivity phenomenon will occur in the electrolyte solution. To avoid that, an air agitator (22) is put into the testing cell (31). The air agitator (22) pushes air into the electrolyte solution to make the electrolyte solution uniform.

EXAMPLE 2

The specimen is a copper substrate covered with nickel-copper coating and nickel coating. The electrolyte solution is 100 ml HCl/l. The program stored in the computer is executed and the following parameters are input:

the testing area of the specimen is 100 mm$^2$, the current is 10 mA, the current efficiency is 100%, the atomic weight, the valence, and the density of the nickel coating respectively are 58.7 g/cm$^3$, 2, and 8.9 g/cm$^3$, the polarization potential is 1 Volt for nickel coating, and 2 Volts for a nickel-copper coating.

Figure 5:
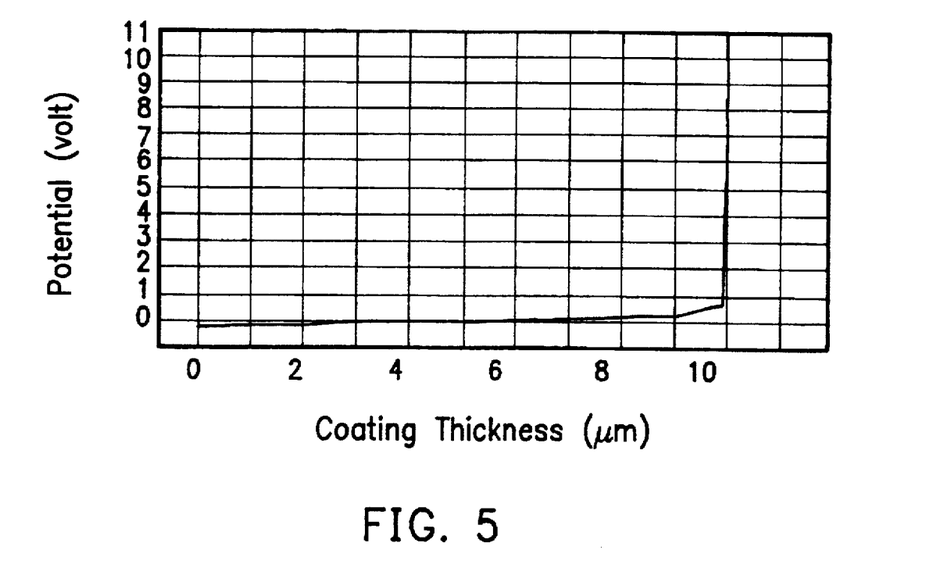
FIG. 5 shows the curve of the potential relative to the coating thickness in example 2.

FIG. 5 shows the curve of the potential relative to the coating thickness. The thickness of the coatings is 9.98 μm for nickel and 0.14 μm for nickel-copper.

Current Efficiency

To measure the current efficiency of electroplating, a specimen is electroplated with a constant current for a predetermined period $T_c$ to form a coating thereon. Then, the coating is electrolyzed with the same constant current. The electroplating period $T_c$, set in advance, and the electrolyzing period $T_a$, counted during the electrolyzing process, are substituted into the following formula [5] to find the current efficiency $E_c$.

$$E_c = \frac{T_a}{T_c} \, 100\% \qquad [5]$$

Figure 6:
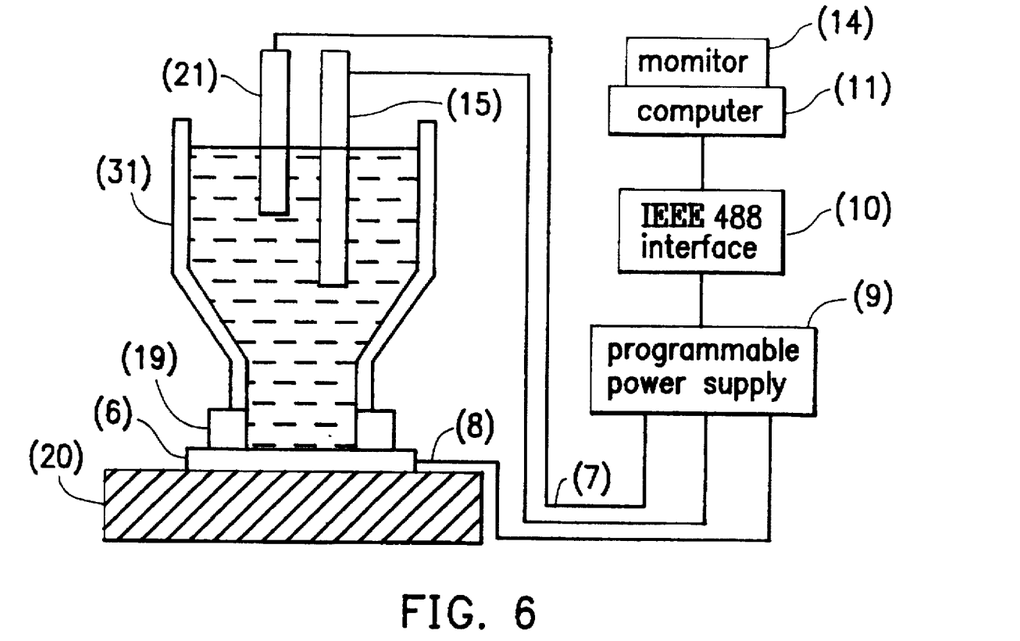
FIG. 6 shows a coating analysis apparatus for analyzing the current efficiency in an electroplating process or a coating analysis apparatus for analyzing corrosion rate of coating according to this invention.

FIG. 6 shows a coating analysis apparatus for analyzing current efficiency during an electroplating process according to this invention. A specimen (6), such as a metal plate, is put on a worktable (20) and a testing cell (31) is put on the specimen (6) with an insulating gasket (19) mounted on its bottom. The size of the insulating gasket (19) can determine the measured area of the specimen (6). A positive terminal of a programmable power supply (9) is electrically connected to an auxiliary electrode (21) through an anode conducting wire (7) to make the auxiliary electrode an anode, while a negative terminal of the programmable power supply (9) is electrically connected to the specimen (6) through a cathode conducting wire (8) to make the specimen a cathode. Also, a reference electrode (15) is put in the testing cell (31) and electrically connected to the programmable power supply (9) to supply a reference potential with respect to both the anode and the cathode. An IEEE 488 interface (10) is electrically connected between the programmable power supply (9) and a computer (11). The computer (11) is provided with a monitor (14) for showing the analyzing results. After the above arrangement is complete, the testing cell (31) is filled with an electroplating solution.

During the electroplating process, the computer (11) controls the programmable power supply (9) through the IEEE 488 interface (10) to supply a constant current $I_{const}$ to electroplate the specimen (6) for the predetermined period $T_c$. As a result, the specimen (6) is covered with a coating.

Figure 7:
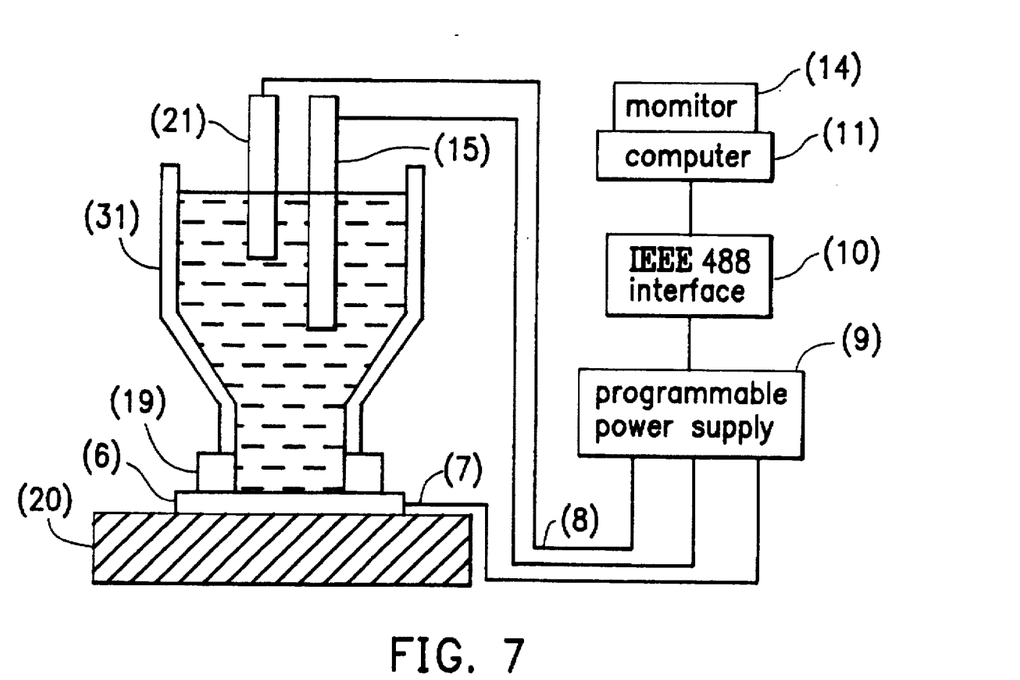
FIG. 7 shows a coating analysis apparatus for analyzing current efficiency in an electrolyzing process according to this invention.

FIG. 7 shows the coating analysis apparatus for analyzing current efficiency during an electrolyzing process according to this invention. It is noted that the specimen (6) has already been covered with the coating. Besides, the negative terminal of the programmable power supply (9) is electrically connected to the auxiliary electrode (21) to make it a cathode through the cathode conducting wire (8) and the positive terminal of the programmable power supply (9) is electrically connected to the specimen (6) to make it an anode through the anode conducting wire (7). Furthermore, the testing cell (31) is filled with an electrolyte solution instead of the electroplating solution.

During the electrolyzing process, the computer (11) controls the programmable power supply (9) through the IEEE 488 interface (10) to supply the same constant current $I_{const}$ to electrolyze the coating of the specimen (6), and at the same time, the programmable power supply (9) converts the potential between the anode and the cathode to a potential signal and sends the potential signal to the computer (11) through the IEEE 488 interface (10). Once the coating entirely dissolves, the potential between the cathode and the anode varies a lot (the potential at the moment is called polarization potential). The computer (11) can detect the potential variation by analyzing the potential signal and cut off the power supply through the IEEE 488 interface (10). At last, the computer (11) calculates the current efficiency according to the formula [5] and displays the results on the monitor (14). A program stored in the computer (11) for analyzing the current efficiency is shown in attached document 3.

EXAMPLE 3

A copper plate is selected as the specimen and is electroplated with nickel coating. Both the electroplating solution and the electrolyte solution are 100 ml HCl/l. The following parameters are input into the computer:

the constant current value is 5 mA, the polarization potential is 1 Volt for the nickel coating and 2 Volts for the copper specimen, the electroplating period is set at 200 seconds.

As a result, the current efficiency of electroplating is 93.8%.

The Corrosion Rate of a Coating

In this embodiment, electrochemical methods are utilized to measure the corrosion rate of a coating. According to the electrochemical methods, a corrosion current is measured and then converted into the corrosion rate. Because these methods are well known to those skilled in the art, a more detailed description is omitted.

Some relative theories are very important and helpful for readers to comprehend this embodiment and are therefore introduced first.

1]. Galvanic Corrosion System, developed by R. S. Munn et al., 1991, supra, can represent the corrosion behaviors and be used for finding the numeral solution thereof.

$$\frac{\sigma}{\rho C} \nabla^2 \phi = \frac{\partial \phi}{\partial t}$$

wherein

σ is electrical conductivity,

ρ is volume mass density,

C is specific electric capacitance, $\nabla^2$ is Laplacian operator,

φ is electric potential, t is time.

This is the potential field equation, or the Fourier equation, describing the electric potential distribution in a conducting medium, such as a conducting electrolyte. If sources or sinks are present, supplying or accepting a charge per unit volume per unit time q, the general field equation becomes:

$$\nabla^2 \phi + \frac{q}{\sigma} = \frac{\rho C}{\sigma} \frac{\partial \phi}{\partial t}$$

Most electrochemical problems are considered to be quasi-state ($\partial/\partial t=0$), and any internally generated current is accounted in the polarization layers of the metallic electrodes as a boundary condition, not in the partial differential equation. Therefore, the Laplace equation governs:

$$\nabla^2 \phi = 0$$

Four boundary conditions, studied by C. Kasper, 1940, supra, are as follows: 1) Dirichlet Boundary Conditions; 2) Neuman Boundary Conditions; 3) Nonlinear Boundary Conditions; 4) Mixed Boundary Conditions. This embodiment relates to the third of these boundary conditions.

2]. A Mixed Potential Theory was developed by J. O. M. Bockris, supra, wherein the corrosion phenomenon on the nonlinear boundary conditions can be represented by Buter-Volmer Equation, $$i_{net} = i_o \left[ \exp\left(\frac{-\beta F \epsilon}{RT}\right) - \exp\left(\frac{(1-\beta)F\epsilon}{RT}\right) \right]$$

or by Tafel Equation, $$\epsilon_a = \frac{RT}{\alpha ZF} \ln i_o - \frac{RT}{\alpha ZF} \ln i_a$$

wherein $i_{net}$ is net current density, $i_o$ is exchange current,

β is transfer coefficient,

F is Faraday's constant,

ε is potential,

R is gas constant,

T is absolute temperature,

α is factor parameter,

Z is valence change, subscript a is anode.

The polarization of metal can be indicated by the following formulas, $$i_m = i_{om} 10^{\epsilon_m/\beta_m}$$

$$\epsilon_m = \beta_m \log\left(\frac{i_m}{i_{om}}\right)$$

$$i_r = i_{or} 10^{\epsilon_r/\beta_r}$$

wherein subscript m is metal dissolution, subscript r is reduction.

When the corrosion rate is controlled by the activation and the polarization of concentration, the polarization of metal can be represented as:

$$\epsilon_m = \beta_m \log\left(\frac{i_m}{i_{om}}\right) + 2.3 \frac{RT}{ZF} \log\left(1 - \frac{i_m}{i_{pass}}\right)$$

$$i_m = \frac{i_{om} 10^{\epsilon_m/\beta_m}}{\left[1 + \left(\frac{i_{om} 10^{(\epsilon_m/\beta_m)}}{i_{pass}}\right)^{k_m}\right]^{1/k_m}}$$

wherein k is a constant affecting the curvature at the transition from Tafel to diffusion-limited behavior, and $i_{pass}$ is passive current density.

$$\epsilon_r = \beta_r \log\left(\frac{i_r}{i_{or}}\right) + 2.3 \frac{RT}{ZF} \log\left(1 - \frac{i_r}{i_l}\right)$$

$$i_r = \frac{i_{or} 10^{\epsilon_r/\beta_r}}{\left[1 + \left(\frac{i_{or} 10^{(\epsilon_r/\beta_r)}}{i_l}\right)^{k_r}\right]^{1/k_r}}$$

wherein $i_l$ i limiting current density.

3]. A Graphical Expressing Method, developed by Evans et al. supra, is based on an (E-log i) diagram to find corrosion current.

4]. Wagner and Trand, 1938, supra, developed a Tafel Extrapolation based on the Mixed Potential Theory for finding the corrosion rate:

$$i_c = i_{oa} \left\{ \exp\left[\frac{Z_a(1-\beta_a)\epsilon_c}{RT}\right] - \exp\left[\frac{-Z_a F \beta_a \epsilon_c}{RT}\right] \right\}$$

-continued $$i_c = i_{oc} \left\{ \exp\left[\frac{Z_c F \beta_c \epsilon_c}{RT}\right] - \exp\left[\frac{-Z_a F(1-\beta_c)\epsilon_c}{RT}\right] \right\}$$

$$i_{net} = i_a - i_c$$

wherein subscript a is anode,
subscript c is cathode, when $\epsilon \gg 0$, $$i_a = i_{oa} \exp\left[\frac{(1-\beta_a)Z_a F \epsilon_a}{RT}\right]$$

$$i_c = i_{oc} \exp\left[\frac{-\beta_c Z_c F \epsilon_c}{RT}\right]$$

$$\log\frac{i_a}{i_{oa}} = \frac{F(1-\beta_a)Z_a \epsilon_a}{RT}$$

$$\frac{\partial \epsilon_a}{\partial \log i_a} = \frac{RT}{Z_a F(1-\beta_a)}$$

thus, the corrosion current $i_{corr}$ is represented as follows:

$$i_{corr} = i_{oa} \exp\left[\frac{(1-\beta_a)Z_a F \epsilon_{corr}}{RT}\right]$$

$$i_{corr} = i_{oc} \exp\left[\frac{-\beta_c Z_c F \epsilon_{corr}}{RT}\right]$$

$$\log i_a = a_a + b_a \epsilon_a$$
$$\log i_c = a_c + b_c \epsilon_c$$
$$a_a = \log i_{oa}$$
$$a_c = \log i_{oc}$$

$$b_a = \frac{Z_a(1-\beta_a)F}{RT} = \frac{\partial \log i_a}{\partial \epsilon}$$

$$b_c = \frac{-Z_c \beta_c F}{RT} = \frac{\partial \log i_c}{\partial \epsilon}$$

and then $$\begin{cases} i_{corr} = \exp[a_a + b_a \epsilon_{corr}] \\ i_{corr} = \exp[a_c + b_c \epsilon_{corr}] \end{cases} \quad [6']$$

Alternatively, the formulas [6'] can be rewritten as follows:

$$T.I_c = \exp[a + b E_{corr}] \quad [6]$$

wherein $T.I_c$ is the Tafel extrapolation corrosion current;
a and b are Tafel constants;
$E_{corr}$ is corrosion potential.

5]. A Method of Linear Polarization was developed by Cao Chu-Nan, supra, wherein the polarization curve of the activation-controlled corrosion system is linear in the region in that the polarization potential is close to the corrosion potential. The corrosion current is derived as follows:

$$i_a = i_{corr} \exp\left[(1-\beta_a)\frac{Z_a F}{RT} \epsilon\right] = i_{corr} \exp\left[\frac{2.3\epsilon}{\beta_a}\right]$$

$$i_c = i_{corr} \exp\left[\beta_c \frac{Z_c F}{RT} \epsilon\right] = i_{corr} \exp\left[\frac{-2.3\epsilon}{\beta_c}\right]$$

when $\epsilon \to 0$, $$\left[\frac{\partial \epsilon}{\partial \log i_a}\right]_{\epsilon \to 0} = \frac{2.3RT}{(1-\beta_a)Z_a F} = B_a$$

$$\left[\frac{\partial \epsilon}{\partial \log i_c}\right]_{\epsilon \to 0} = \frac{2.3RT}{\beta_c Z_c F} = B_c$$

thus $$i_{corr} = \frac{B_a B_c}{(B_a + B_c)} \left[\frac{i_{app}}{\epsilon}\right] \quad [7']$$

Alternatively, $$L.I_c = \frac{B_a B_c}{(B_a + B_c)} \left[\frac{i_{app}}{\epsilon}\right] \quad [7]$$

wherein $L.I_c$ is the linear polarization corrosion current;
$B_a$ and $B_c$ are transfer coefficients;
$i_{app}$ is current;
$\epsilon$ is potential.

6]. A Method of Polarization Resistance was developed by Stern and Geary, supra, wherein the average between the transfer coefficients $B_a$ and $B_c$ is 0.12V. Therefore, $$i_{corr} = \left[\frac{B_a B_c}{2.3(B_a+B_c)}\right]\left[\frac{i_{app}}{\epsilon}\right] = \left[\frac{B_a B_c}{2.3(B_a+B_c)}\right]\left[\frac{1}{R_p}\right] \quad [8']$$

$$= \left[\frac{0.12 \times 0.12}{2.3(0.12+0.12)}\right]\left[\frac{1}{R_p}\right] = \frac{0.026}{R_p}$$

Alternatively, $$R.I_c = \frac{0.026}{R_p} \quad [8]$$

wherein $R.I_c$ is polarization resistance corrosion current;

$$R_p = \left[\frac{\partial \epsilon}{\partial i}\right]_{i \to 0} = \frac{B_a B_c}{(B_a+B_c)i_0} \;;$$

$R_p$ is polarization resistance;
$i_0$ is exchange current.

Please refer back to FIG. 6, which can also show a coating analysis apparatus for analyzing the corrosion rate of a coating (or metal, alloy) according to this invention. A specimen (6) with its upper surface covered with a coating is put on a worktable (20), and a testing cell (31) with an insulating gasket (19) mounted on its bottom is put on the specimen (6). It is noted that the size of the insulating gasket (19) can determine the testing area of the specimen (6).

A reference electrode (15) and an auxiliary electrode (21) are put into the testing cell (31), wherein the reference electrode (15) is electrically connected to a programmable power supply (9). A positive terminal of the programmable power supply (9) is connected to the auxiliary electrode (21) through an anode conducting wire (7) to make the auxiliary electrode an anode, and a negative terminal of the programmable power supply (9) is electrically connected to the specimen (6) through a cathode conducting wire (8) to make the specimen a cathode. Furthermore, the programmable power supply (9) is electrically connected to a computer (11) through an IEEE 488 interface (10). The computer (11) is provided with a monitor (14) for showing the analyzing results. After the above arrangement is done, the testing cell (31) is filled with a corrosion solution. The programmable power supply (9), the anode conducting wire (7), the auxiliary electrode (21), the corrosion solution, the specimen (6) and the cathode conducting wire (8) thus form a circuit.

Some data need to be input into the computer (11) before the measuring process starts. The data include the testing area of the specimen, the initial applied potential, the final applied potential, the scan rate of the programmable power supply and the potential of the reference electrode.

During the measuring process, the computer (11) controls the programmable power supply (9) through the IEEE 488 interface (10) to supply the initial applied potential and varies the applied potential at a predetermined rate (i.e. the scan rate). At the same time, the programmable power supply (9) converts the current in the circuit to a current signal and sends the current signal back to the computer (11) through the IEEE 488 interface (10) so that the computer (11) can use the above-mentioned formulas [6], [7], and [8] to calculate the Tafel extrapolation corrosion current $T.I_c$, the linear polarization corrosion current $L.I_c$ and the polarization resistance corrosion current $R.I_c$. The measuring program and the analyzing program, stored in the computer (11), are respectively shown in the attached documents 4.

EXAMPLE 4

The experiments were conducted using the Cu-Ni-Sn-P alloy as the specimen. The specimen is mechanically polished and finished using #100, #200, #300, and #400 grit emery paper, then, rinsed in distilled water and acetone, and finally, dried by air. The testing area of each of the specimens defined by the insulating gasket is 3.14 mm². The corrosion solution is 0.3% of NaCl aqueous. A platinum electrode and a saturated calomel electrode (SEC) are respectively treated as the auxiliary electrode and the reference electrode. The applied potential is varied from −1 Volt to +1 Volt with respect to the reference electrode at a rate of 2 mVolt/sec. As a result, the Tafel extrapolation corrosion current $T.I_c$ is 2.225919 mA/cm², the linear polarization corrosion current $L.I_c$ is 0.10647 mA/cm² and the polarization resistance corrosion current $R.I_c$ is 0.11589 mA/cm². It is obvious that the measuring result of $T.I_c$ is far away from the other measuring results $L.I_c$, $R.I_c$. Thus, the measuring result of $T.I_c$ is inaccurate and should not be considered. The other measuring results $L.I_c$, $R.I_c$ can be utilized to estimate the corrosion rate. For example, the average of the two measuring values $L.I_c$, $R.I_c$ may be chosen as a estimating value.

The example 4 indicates that some measuring results are inaccurate now and then. Conventional analysis apparatuses can merely supply one kind of analyzing result. Therefore, the user can not judge if the analyzing results are correct. However, the present invention does not have such a problem.

Although this invention has been described in its preferred forms and various examples with a certain degree of particularity, it is understood that the present disclosure of the preferred forms and the various examples can be changed in the details of construction. The scope of the invention should be determined by the appended claims and not by the specific examples given.

What is claimed is:

1. A coating analysis apparatus for analyzing internal stress within a coating on one surface of a specimen that has two ends with an electroplating solution, comprising:

a testing cell filled with the electroplating solution;

a fixture mounted in the testing cell for fixing one end of the specimen such that one end of the specimen is fixed by the fixture and the other end of the specimen is free;

a metallic object mounted in the testing cell;

a programmable power supply comprising a positive terminal coupled with the metallic object and a negative terminal coupled with the specimen for supplying current to electroplate the specimen;

a noncontact displacement sensor mounted beside the free end of the specimen and coupled with the programmable power supply for sensing displacement of the free end of the specimen and generating and sending a displacement signal to the programmable power supply; and a microprocessor coupled with the programmable power supply for controlling the programmable power supply to supply the current and for receiving the displacement signal from the programmable power supply as well as for calculating the internal stress within the coating.

* * * * *